(12) United States Patent
Yoon

(10) Patent No.: US 6,506,599 B1
(45) Date of Patent: Jan. 14, 2003

(54) METHOD FOR CULTURING LANGERHANS ISLETS AND ISLET AUTOTRANSPLANTATION ISLET REGENERATION

(76) Inventor: Tai-Wook Yoon, 51-72 Ho Yeonhee 3-Dong, Seodaemoon-Ku Seoul (KR)

( * ) Notice: Subject to any disclaimer, the term of this patent is extended or adjusted under 35 U.S.C. 154(b) by 0 days.

(21) Appl. No.: 09/418,765

(22) Filed: Oct. 15, 1999

(51) Int. Cl.$^7$ .............................. C12N 5/08; C12N 5/06; C12N 5/02
(52) U.S. Cl. ...................... 435/370; 435/366; 435/370; 435/377; 435/383; 435/353
(58) Field of Search ...................... 424/93.7; 435/370, 435/366, 353, 383, 377

(56) References Cited

U.S. PATENT DOCUMENTS

| | | | | |
|---|---|---|---|---|
| 5,116,753 A | * | 5/1992 | Beattie et al. ............ | 435/240.2 |
| 5,693,483 A | * | 12/1997 | Staunton et al. ............... | 435/29 |
| 5,888,705 A | * | 3/1999 | Rubin et al. ................ | 435/366 |

FOREIGN PATENT DOCUMENTS

KR 136848 1/1998

OTHER PUBLICATIONS

Brendel et al. Transplanation. 1994. vol. 3, No. 5, pp. 427–435.*
Oberg–Welsh et al. Molecular and Cellular Endocrinology. (1997). 126:125–132.*
Freshey R.I. In: Culture of animal cells. A manual of basic Technique. 1987. Alan R. Liss, Inc. Second Edition. pp. 74–84.*
Levine et al. Cell Transplantation. 1994. vol. 3, No. 4, pp. 307–313.*

* cited by examiner

Primary Examiner—Sandra E. Saucier
Assistant Examiner—Vera Afremova
(74) Attorney, Agent, or Firm—Seed IP Law Group PLLC

(57) ABSTRACT

A method for culturing Langerhans islets to obtain an amount sufficient for transplant and autotransplant is disclosed. The islets are cultured in a culture serum (rat/human) medium which is supplemented with radical scavengers, growth factors, a matrix material, nerve growth factor, cell migrating/scattering factors and anti-integrin β1 antibody at proper the time during the culturing process. The medium is supplemented with radical scavengers and growth factors for the first time and then further supplemented with matrix material, radical scavengers, nerve growth factor and the growth factors around 12–24 hours after culturing. Thereafter, the medium is supplemented with growth factors, cell migrating/scattering factors and anti-integrin β1 antibody at 4–5 days into the culturing process. The culturing process is conducted for an extended period of time, so that any latent red blood cells are eliminated from the islet culture. The islets then continue to proliferate to produce an amount of islets which is sufficient for transplantation into a diabetic patient, including a human, to provide extended normoglycaemia and islet regeneration to fully treat diabetes mellitus without the growth of fibroblasts.

5 Claims, 16 Drawing Sheets

Blood cells were released from islets which were incubated overnight at 37°C.  X100

Islet was incubated overnight at 37°C without radical scavenger.  Many islet cells were dead on the surface of the islet.  X100

Islet cells were incubated overnight at 37°C with radical scavenger. There were no dead islet cells on the surface of islet. X100

The islets were incubated with VeGF, IGF-1, and IGF-2. Islets look intact without dead cells on the surface. X200

This showed the islets on the 2nd day of proliferation. Islets have very smooth surface and high viability.

The islet was cultured in the medium supplemented with anti-integrin $\beta_1$-antibody on 3rd or 4th day. Growing cells appeared on the surface of the islet, which then looks like a mulberry. X100

The islet was cultured in the presence of migrating factors (ex. HGF) on 3rd or 4th day. It seems to spread horizontally. X100

Front shape (A) and lateral shape (B) showed thick and long buds from the islet in 10th day. This proved that islet can grow in all directions. X320

Showed human islet that was proliferated *in vitro* for 8 days by using rat islet proliferation methods.

This shows the increasing DNA content of *in vitro* proliferating SD rat islets with days.

This showed the process of fibroblast development and its depletion from the islets. Many fibroblasts grew out from islet during islet proliferation (A) even though the islets looked pure when they were collected. The fibroblasts were removed mostly (B) and completely (C) from the islets.

1650 (IEQ 2750) and 1350 (IEQ 2400) fresh rat islets were translated into liver of rat via hepatic portal vein. Blood glucose levels were measured and plotted with days to make graph. Circle points represent blood glucose level of rat transplanted with 1650 fresh islets and triangle points, that with 1350 fresh islets.

This showed the changes of blood glucose levels of rats transplanted with 500 proliferated islets with days, 0 day, islets were transplanted.

This graph shows the profiles of nude mice blood glucose levels controlled by transplantation of fresh islets at different number to determine minimum required number of fresh islets for recovery and maintenance of normal blood glucose level from hyperglycemia. 500, 600, 800, 1000, and 1200 mean transplanted islet number.

Photograph showing fresh islet transplanted into spleen. The islet was stained with insulin-specific staining method. X200 magnification.

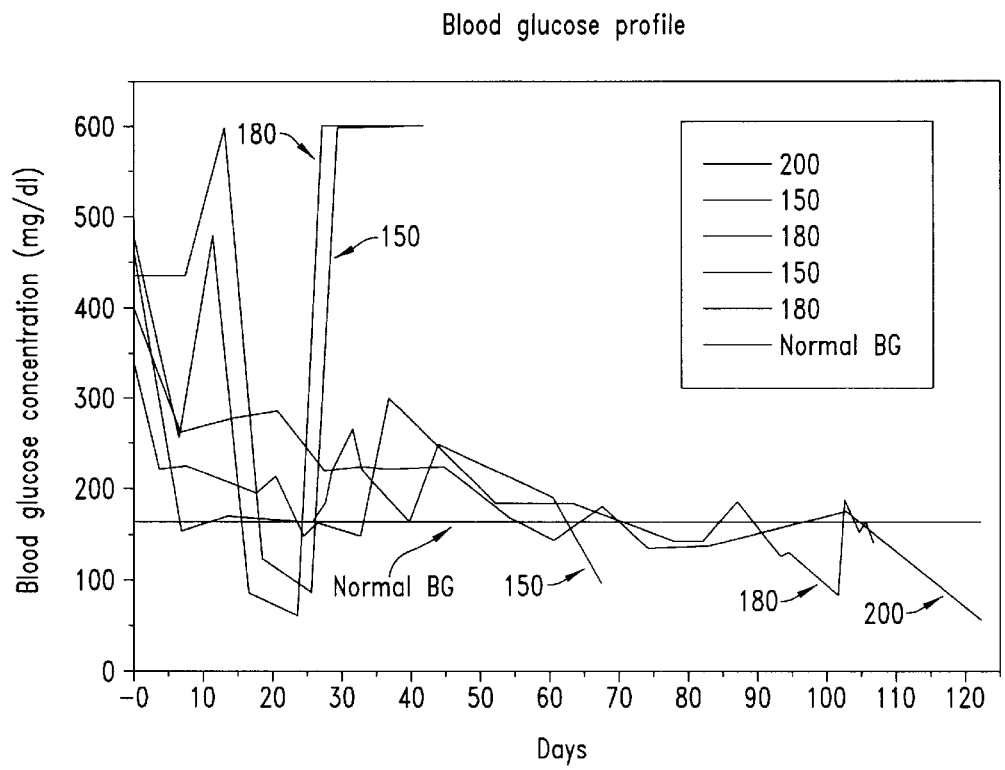

This is the blood glucose profile of STZ-induced diabetic nude mice transplanted with different number of *in vitro* proliferated SD rat islets, and that of normal nude mice without diabetes. The islets were transplanted into the spleen. The number of transplanted islets is expressed by a number (200 islets; 150 islets; 180 islets; normal BG-blood glucose concentration of normal nude mice without diabetes.)

*Fig. 17*

Photograph showing the transplanted islet stained deeply brown in the spleen. X400 magnification.

METHOD FOR CULTURING LANGERHANS ISLETS AND ISLET AUTOTRANSPLANTATION ISLET REGENERATION

BACKGROUND OF THE INVENTION

1. Field of the Invention

The present invention relates to a method for culturing the Langerhans islets suitable for transplantation. More particularly, the present invention relates to a culturing method by which the Langerhans islets can be proliferated in volume, and the fact that proliferated islet autotransplantation can stimulate islet regeneration via islet replication and neogenesis, leads to a perfect diabetes cure.

2. Description of the Prior Art

Diabetes mellitus (usually referred to simply as diabetes) is a complex disease characterized by a grossly abnormal pattern of carbohydrate metabolism resulting from impaired insulin secretion and/or effectiveness. The incidence of diabetes in industrialized countries is about 10%. Indeed, diabetes is the most common serious metabolic disease in the world, it affects hundreds of millions.

Diabetes may be classified as insulin-dependent diabetes or noninsulin-dependent diabetes. An absence of or insufficient intrinsic insulin is a characteristic of insulin-dependent diabetes. Some diabetics have a normal or even higher than normal level of insulin in their blood, but they are quite unresponsive to the hormone. This form of the disease, known as non-insulin-dependent diabetes, typically develops later in life than does the insulin-dependent form. However, the diabetes-causing mechanism with which these two types can be discriminated has yet to be revealed.

For treatment, insulin-dependent diabetics should continue to receive exogenous insulin because their capacity of producing insulin is greatly lowered. However, it is virtually impossible to continuously and properly provide insulin in response to patient's physiological demands. What is more difficult, the body has an insulin concentration gradient such that the insulin concentration is decreased in order of: the hepatic portal vein, the liver, the hepatic vein, the aorta and the muscle, but an injection of exogenous insulin does not result in such a concentration gradient, which then causes side effects.

The β-cells of the Langerhans islets secrete insulin and 11 other materials. Thus, an injection of only insulin can decrease the blood glucose level, but cannot prevent glucopenia and other complications. Since one of the objectives in the treatment of diabetes is to lower the blood glucose level, blood glucose lowering agents are often employed. These lowering agents, however, should not be prescribed for an extended period of time because they result in resistance. Moreover, blood glucose lowering agents were found to cause serious side effects.

Insulin, as mentioned above, is able to lower blood glucose level as well as gives much lower resistance than do blood glucose lowering agents. However, the necessary amount of insulin varies with a patient's conditions so that it is very difficult to timely administrate proper dosage of insulin. Upon improper administration of insulin, anti-insulin antibodies may be formed, making diabetes worse.

For curing diabetes, tissue transplantation has recently been of great interest. For example, the pancreas or Langerhans islets are transplanted into a patient who suffers from diabetes to provide a controlled amount of insulin which is necessary for the patient.

In such cases, however, immune rejection is always problematic and must be considered. When the immune rejection occurs, immune suppressors are administered to the patients. In addition, the number of donors are not sufficient relative to the demand.

The treatment of diabetes by insulin administration was first conducted in 1921 by Banting and Best, but they failed to cure the disease because of a diabetic complication. In 1966, Lillihei of Minnesota University first transplanted a portion of the pancreas into a diabetic patient. By 1977, 57 patients had been subjected to the transplantation. However, less than 10% of them survived for one year or more. Recent development of immune suppressors has increased the survival rate of pancreas or kidney transplant recipients up to 70%. For Langerhans islet transplantation, the survival rate amounts up to 90%.

The first thing into which account is taken is the histocompatibility between donor and recipient. If tissue transplantation is performed between two persons who have different histocompatibility, an immune rejection occurs, leading to the destruction of the transplanted islets at the worst. Generally, 50 donors are needed to discover the necessary histocompatibility for one recipient. If fresh islets are transplanted, a large quantity of fibrous tissues grow out from freshly isolated Langerhans islets and divide and surround them if transplanted, so that the ability of the β-cells to secrete insulin in response to a stimulus declines greatly.

SUMMARY OF THE INVENTION

In approaching the present invention, the present inventors considered the following:

First, in order for cells or cell groups to proliferate in vitro, they must contain stem cells or progenitor cells therein and be in undifferentiated states. Fortunately, since many stem cells or progenitor cells exist in Langerhans islets, it is highly possible to proliferate undifferentiated Langerhans islets in vitro.

Next, MHC class II antigens, which cause immune rejection, must be absent in the proliferated Langerhans islets and thus, if the blood cells, rich in MHC class II antigens, are eliminated from Langerhans islets, the immune rejection can be greatly reduced in the islet allotransplantation. The longer the islets remain in the culture and proliferate, decreases the immune rejection response.

Finally, fibrous tissues are developed from the crude islets and must be able to be easily removed from the in vitro proliferated islet.

Taking advantage of the above three points, the present inventors tried to proliferate in vitro the Langerhans islets with the aim of preparing them so as to be easily and successfully transplanted in the host for the long term treatment of diabetes.

When the Langerhans islets were grown in a monolayer culture method, they proliferated at a rate of, at most, 80%. However, they poorly secreted insulin so that it was impossible to control the level of the blood glucose. The islets should proliferate at least 5-fold for successful transplantation.

Intensive and thorough research repeated by the present inventors resulted in the discovering that upon in vitro culture in media containing various biochemical materials, the Langerhans islets isolated from rats proliferate at high rates sufficient to be applied for transplantation, release the blood cells from themselves so as to greatly reduce the immune rejection, and function well enough so as to successfully continue to secrete insulin after transplantation according to the present invention.

Therefore, it is an object of the present invention to provide a method for proliferating the Langerhans islets in a suitable state for transplantation, whereby a greatly enhanced treatment effect for diabetes can be brought about.

In accordance with the present invention, there is provided a method for proliferating the Langerhans islets, in which a culture medium is supplemented with radical scavengers, growth factors, a matrix material, nerve growth factor, cell migrating/scattering factors (such as HGF) anti-necrosis factors or antiapoptosis factors (such as IGF 1, IGF 2, VeGF) and a cytoskeleton activator (anti-integrin β1 antibody) at proper culture times and the proliferation is conducted for an extended period of time, so that the Langerhans islets are depleted of the blood cells and also proliferate sufficiently in order to be suitable for transplantation.

The present inventions are directed to a method for in vitro culturing and proliferating isolated Langerhans islets endocrine cells so as to be suitable for transplantation. To initiate the proliferation viable Langerhans islets endocrine cells including cells capable of differentiating into insulin producing cells are collected and placed in a first culturing medium comprising a basal medium supplemented with serum, at least one radical scavenger selected from the group consisting of nicotinamide, mannitol or superoxide dismutase; at least one growth factor selected from the group consisting of: insulin transferrin selenite-complex (ITS-complex), epidermal growth factor (EGF), platelet derived growth factor (PDGF), thrombin, Linoleic Acid-BSA, hydrocortisone and progesterone, and at least one antinecrosis or antiapoptosis factor selected from the group consisting of. IGF 1, IGF 2, VeGF and culturing the Langerhans islets endocrine cells including cells capable of differentiating into insulin producing cells for a period of about one day in the first culturing medium to form a first culture growth. The first culture growth is collected and incubated at room temperature in fresh DMEM or serum free basal medium with anti-integrin β1 antibody for 45~120 minutes to form a second culture growth.

The second culture growth is then suspended in a matrix material to provide a 3-dimensional culture growth environment and a second culturing medium comprising the supplemented basal medium and further including, at least, another growth factor is added thereto and then culturing proceeds for 1 or 2 days to provide a third culture growth dispersed in the matrix material.

A third culturing medium for culturing the third culture growth in the matrix material is provided and comprises the supplemented basal medium but without VeGF, and optionally adding to the third culturing medium NGF and HGF if the islets of the third culture growth appeared thick and the center of the islets appeared dark, or optionally adding to the third culturing medium NGF and anti-integrin β1 antibody if the islets appeared too spread out and then culturing for a period of about one or two days to form a fourth culture growth. The islets are then collected from the matrix material, placed in a suitable vessel and an enzyme such as dispase is added to the collected islets and to loosen or enable removal of any adhering gel and then incubated for about 10 minutes to provide an incubated product. The incubated product is then aspirated back and forth numerous times causing the gel acted on by the dispase to be removed from the islets thereby exposing the fibroblasts to the force created during the back and forth aspiration which appears to cause the fibroblasts to become separated from the surface of the islets to prepare fibroblast free islets.

The above process takes about 7 days and can be repeated as follows. A fourth culturing medium comprising the basal medium supplemented with serum, insulintransferrin-sodium selenite (ITS), Linoleic Acid-BSA, thrombin, EGF, nicotinamide, VeGF, IGF-1, IGF-2, superoxide dismutase and mannitol is provided and then the fibroblast free islets are cultured for about 8–12 hours to provide a fifth culture growth. The fifth culture growth is collected and cultured in a fifth culturing medium comprising DMEM with anti-integrin β1 antibody for 45~120 minutes at room temperature to form a sixth culture growth. The sixth culture growth is then suspended in a matrix material to provide a 3-dimensional culture growth environment and a sixth culturing medium comprising the supplemented basal medium and further including, at least, another growth factor is added thereto and then cultured for 1 or 2 days to provide a seventh culture growth dispersed in the matrix material.

A seventh culturing medium which comprises the supplemented basal medium without VeGF, and optionally adding to the third culturing medium NGF and HGF if the islets of the third culture growth appeared thick and the center of the islets appeared dark, or optionally adding to the third culturing medium NGF and anti-integrin β1 antibody if the islets appeared too spread out is provided for culturing the seventh culture growth dispersed in the matrix material for a period of about one or two days to form an eighth culture growth. The islets are then collected from the matrix material and an enzyme, such as dispase, is added to the collected islets and to any adhering gel and incubated for about 10 min. to provide an incubated product. The incubated product is aspirated back and forth numerous times causing the gel acted on by the enzyme to be removed form the islets thereby exposing the fibroblasts, if any, to the force created during the back and forth aspiration causing the fibroblasts to become separated from the surface of the islets to prepare an increased number of fibroblast free islets.

In the present method it is preferred that the serum used in the medium is obtained from the same species as that of the Langerhans islets to be proliferated. Thus, where the Langerhans islets are from a rat or human, the serum used is also rat, human serum, respectively, preferably the percent of serum in the medium is about 10%. The growth factor added to the second and sixth culturing medium is preferably pituitary extract.

The method of the present invention also includes using viable Langerhans islets endocrine cells including cells capable of differentiating into insulin producing cells for proliferation which are derived from a patient for proliferation according to the present invention which are then used for autotransplantation back into the same patient. This results in regeneration of the islets in the patient as described below.

The present invention also includes a method for removing fibroblasts growing from the surface of in vitro proliferated Langerhans islets by providing a plurality of proliferated islets having fibroblasts growing therewith in a gel matrix. The islets are collected from the gel matrix, along with the fibroblasts which are growing with the islets. An enzyme, such as dispase, is added to the collected islets and to any gel adhering to the surface of the collected islets and then this is incubated to provide an incubated product. The incubated product is then aspirated back and forth numerous times causing the gel acted on by the dispase to be removed from the islets thereby exposing the fibroblasts to the force being created during the back and forth aspiration which causes the fibroblasts to become separated from the surface of the islets to prepare fibroblast free islets.

The present invention also includes the culture product of proliferated fibroblast free islets produced by the method according to the present invention and the use of the proliferated fibroblast free islets produced by the method according to the present invention in treating diabetes mellitis by transplanting the proliferated Langerhans islets endocrine cells into a patient suffering from diabetes mellitis. In addition, the present invention further includes the use of the proliferated fibroblast free islets from a patient produced by the method according to the present invention to treat diabetes mellitis and to regenerate islets in the patient by autotransplanting the proliferated Langerhans islets endocrine cells into the patient suffering from diabetes mellitis.

BRIEF DESCRIPTION OF THE DRAWINGS

The above and other objects and aspects of the invention will become apparent from the following description of embodiments with reference to the accompanying drawings in which:

FIG. 17 plots 150–200 proliferated islets transplanted into the spleens STZ-induced diabetic mice against time in days.

DETAILED DESCRIPTION OF THE INVENTION

Figure 1:
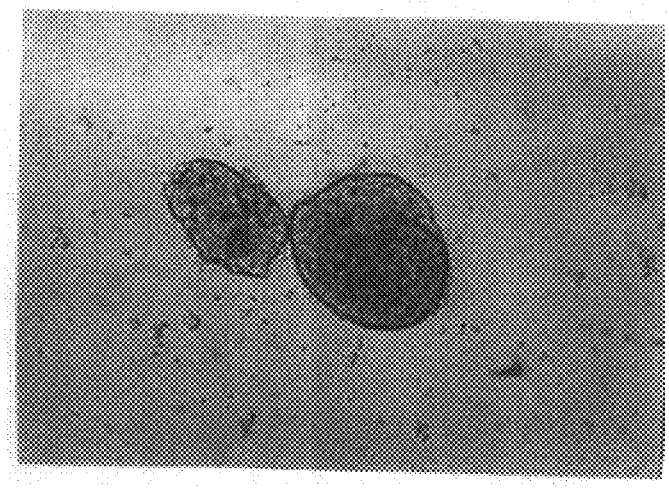
FIG. 1 is a photograph magnified 100 times (×100) showing blood cells released from islet after 24 hour incubation at 37° C.
Figure 2:
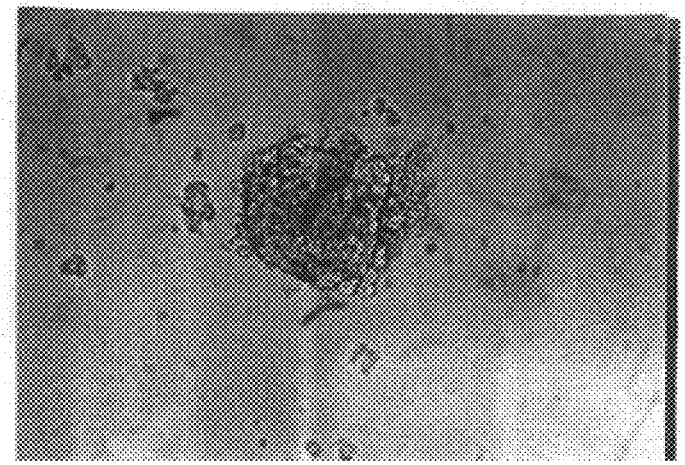
FIG. 2 is a photograph (×100) showing the Langerhans islets which are cultured in the absence of radical scavengers.
Figure 3:
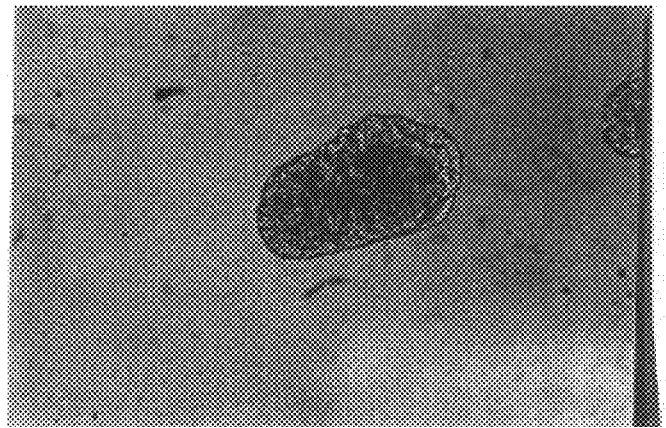
FIG. 3 is a photograph (×100) showing the Langerhans islets which are cultured in the presence of a radical scavenger.
Figure 4:
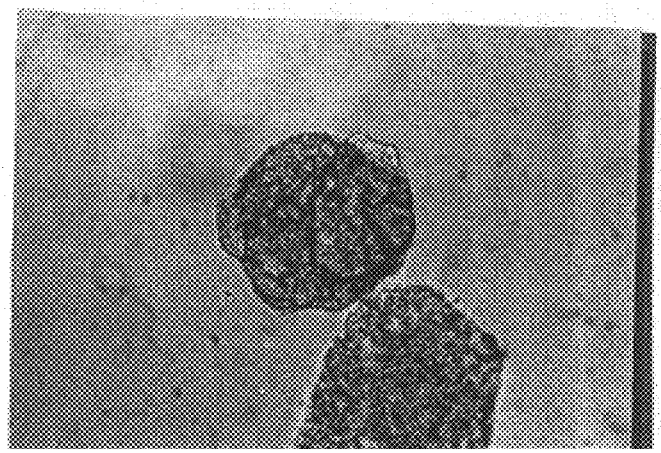
FIG. 4 is a photograph (×200) showing islets which were incubated in a supplemented medium (VeGF, IGF-1, IGF-1)
Figure 5:
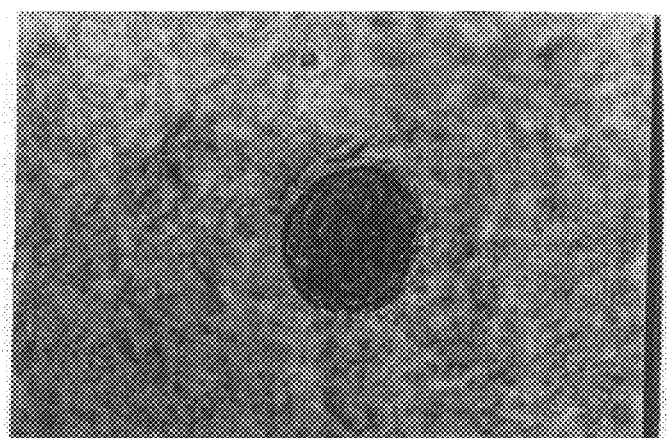
FIG. 5 is a photograph showing the islets on the second day of proliferation.
Figure 6:
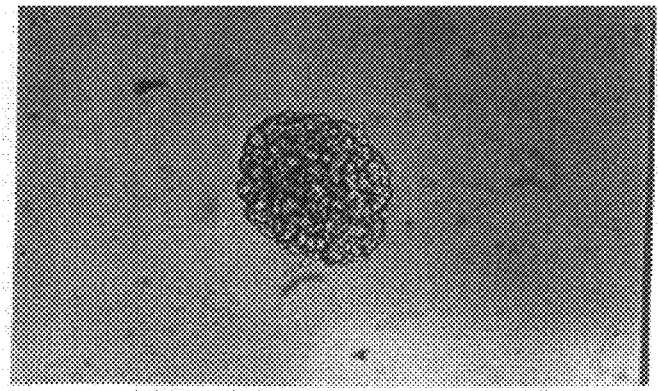
FIG. 6 is a photograph (×100) showing the lateral growth of the Langerhans islets which are proliferated in the medium containing anti-integrin β1 antibody on the 3rd or 4th day.
Figure 7:
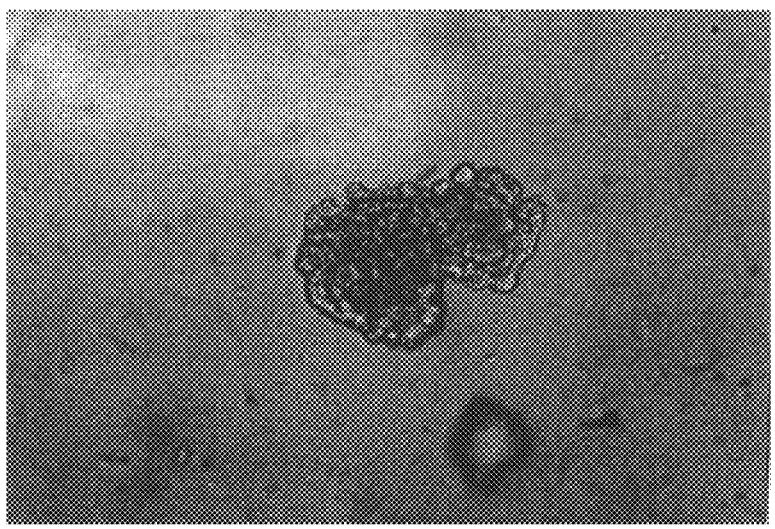
FIG. 7 is a photograph (×100) showing an islet cultured in the presence of migrating factors, showing horizontal growth or spreading of the islet, for example HGF, on the 3rd or 4th day.

To better illustrate the present invention FIGS. 1 through 18 are presented and described below. FIG. 1 shows the islet cells with released red blood cells after being incubated for 24 hours at 37° C. in a medium of rat serum. FIGS. 2 and 3 show the difference when culturing in the absence of and the presence of radical scavengers, respectively. FIG. 4 shows islets which were incubated in a medium supplemented with VeGF, IGF-1 and IGF-2 to increase islet viability. The supplements function as antiapoptotic and anti-necrotic factors. The islets are intact without dead cells on the surface. FIG. 5 is a photograph showing the islets on the second day of proliferation with the islets having a smooth surface and high viability. The medium used in FIG. 6 included anti-integrin β1 antibody and shows growing cells appearing on the surface of the islet. FIG. 7 shows the effect of adding a migrating factor(s), for example, hepatocyte growth factor (HGF), to the medium which appears to cause the islet to spread horizontally.

Figure 8A:
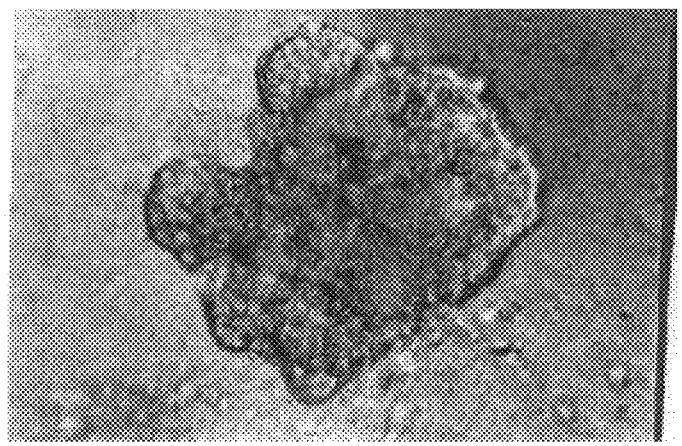
FIGS. 8A and 8B are photographs showing the islet growing in all directions after proliferating for 10 days according to the method of the present invention.
Figure 8B:
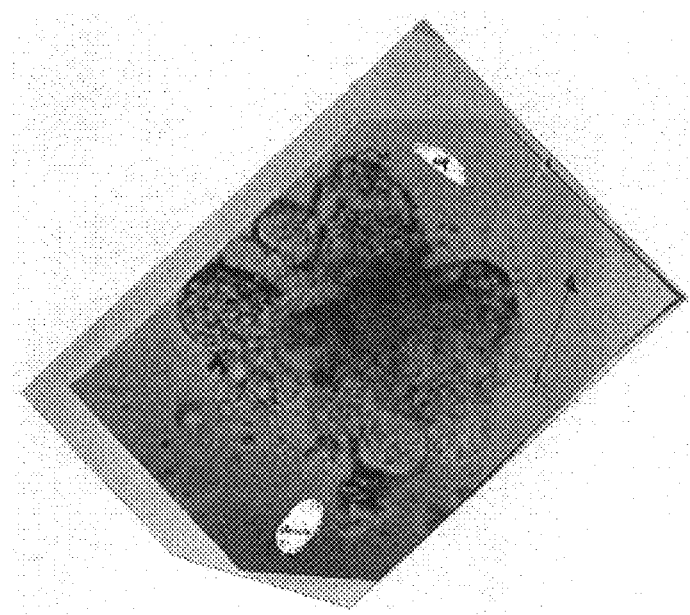
Figure 9:
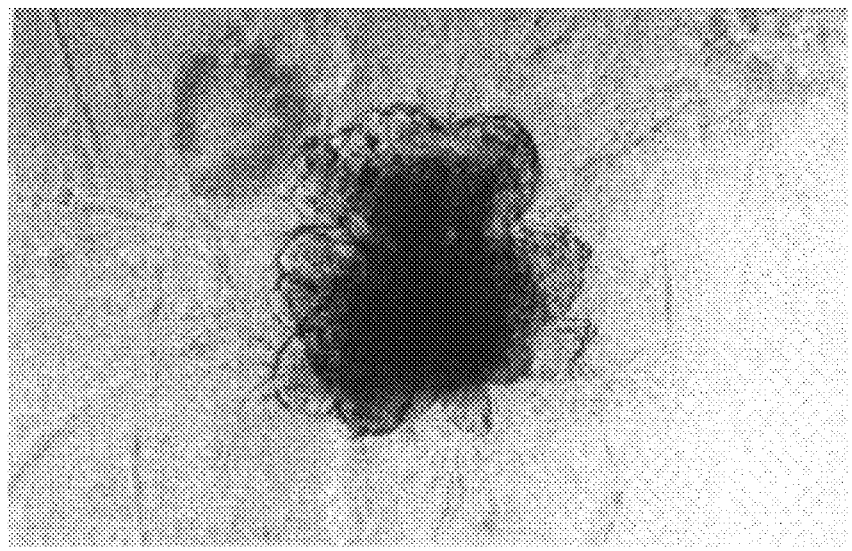
FIG. 9 is a photograph showing a human islet proliferated in vivo for a period of 8 days in the presence of human serum.
Figure 10:
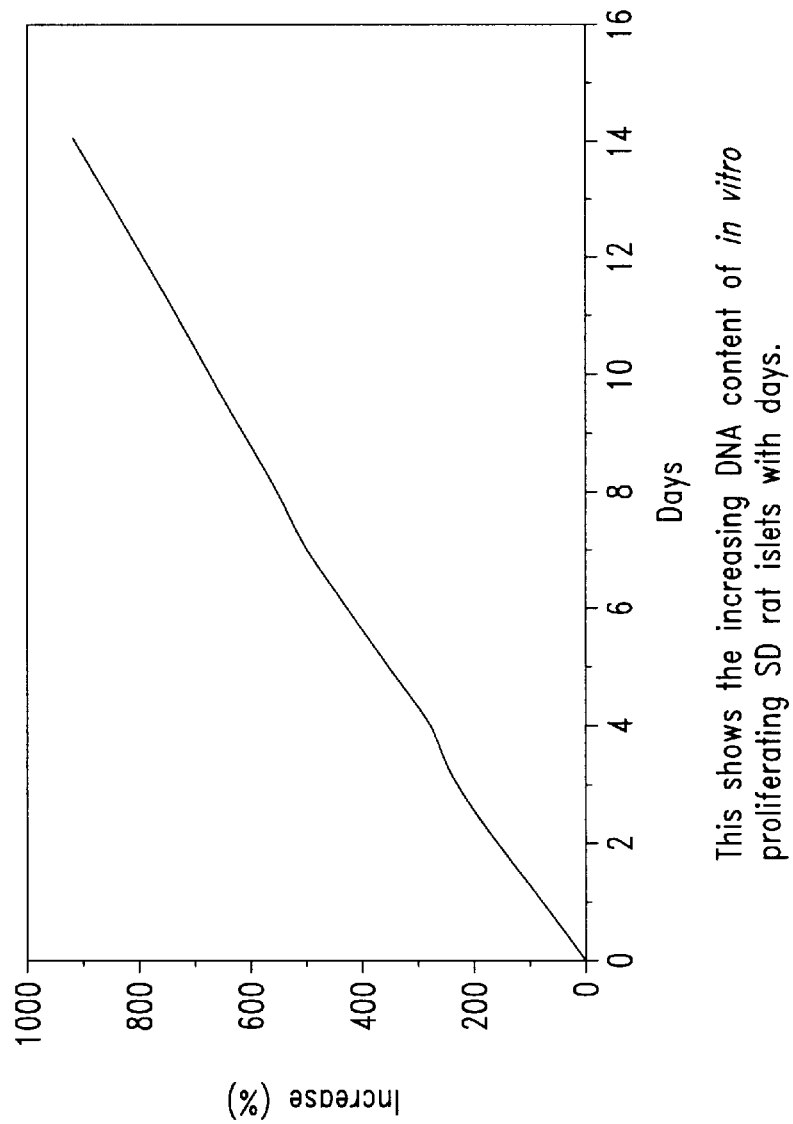
FIG. 10 is a graph showing the change in the DNA amount of the Langerhans islets with culturing time in days.
Figure 11A:
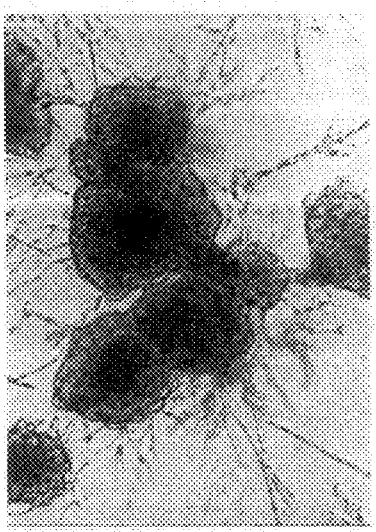
FIGS. 11A, 11B and 11C show the process of fibroblast development and its depletion from the islets. Many fibroblasts grew out from islet during islet proliferated (FIG. 11A) even though the islets looked pure when they were collected. The fibroblasts were almost all removed (FIG. 11B) and completely removed (FIG. 11C) from the islets.
Figure 11B:
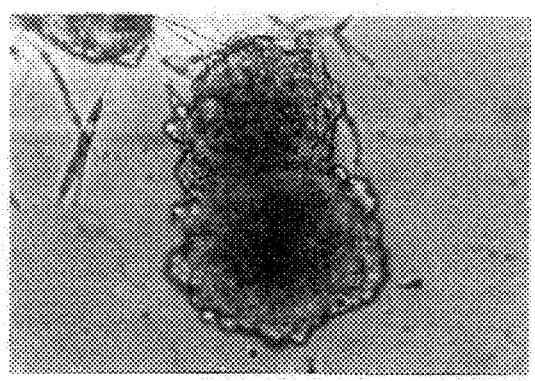
Figure 11C:
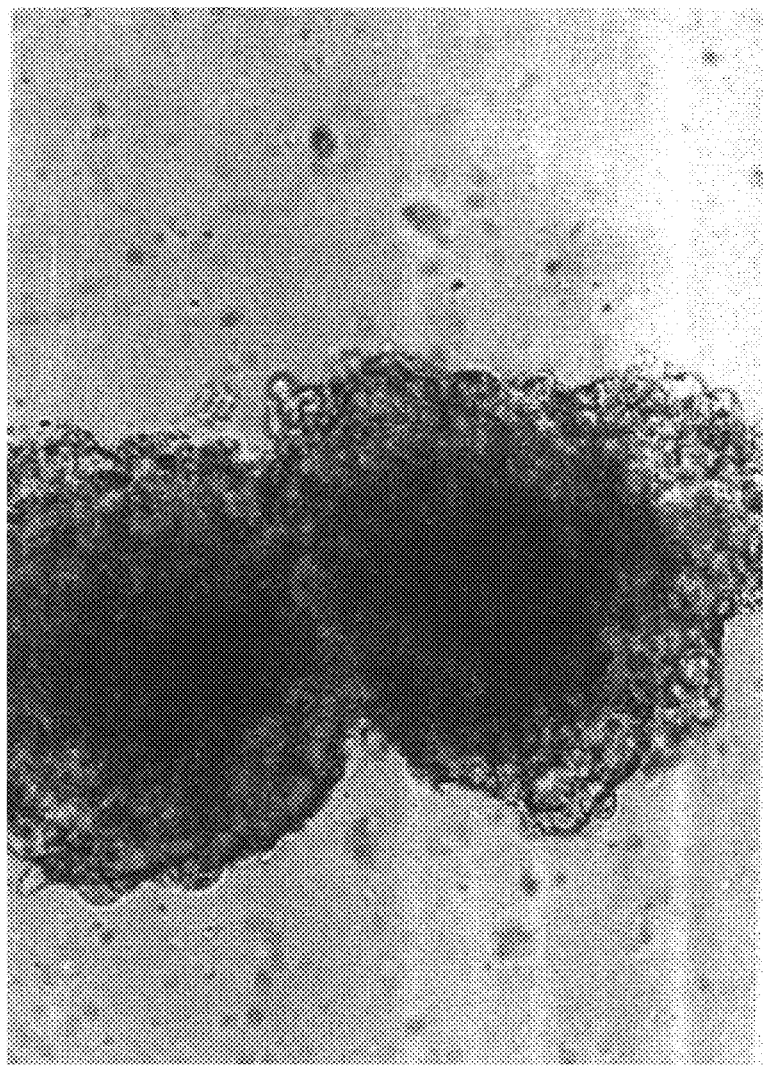
Figure 12:
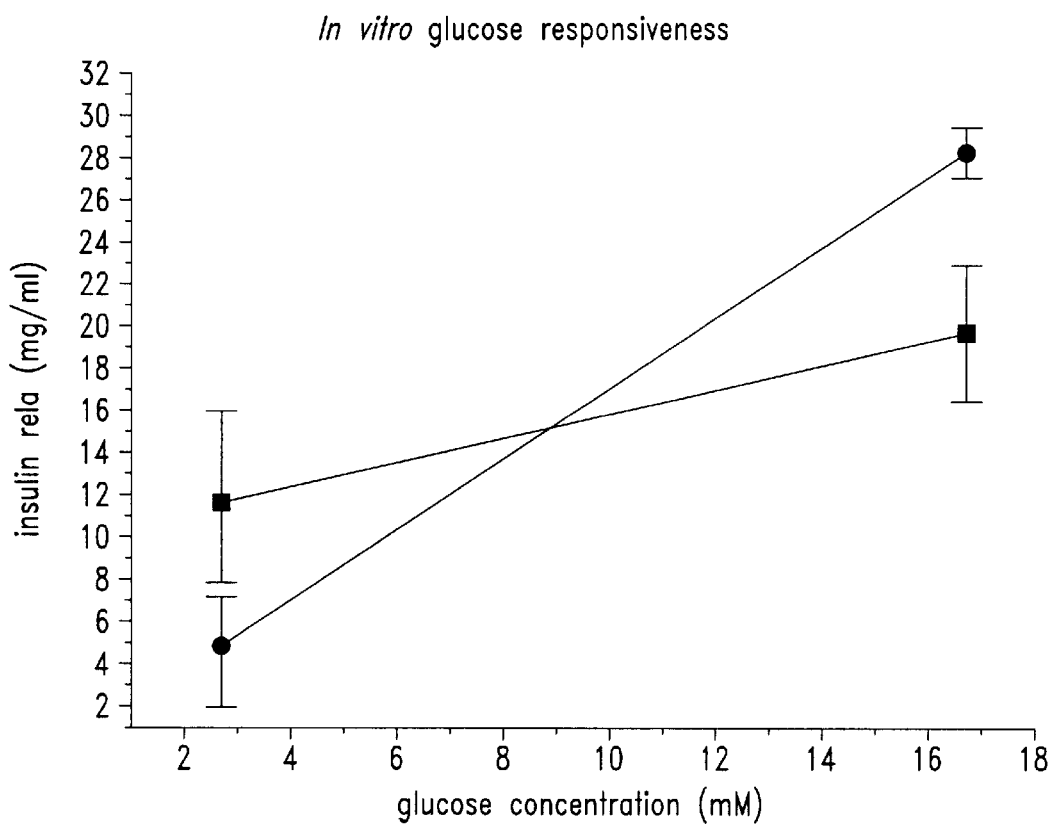
FIG. 12 shows the in vitro functions (glucose-response) of fresh (square) and proliferated (circle) islets.
Figure 13:
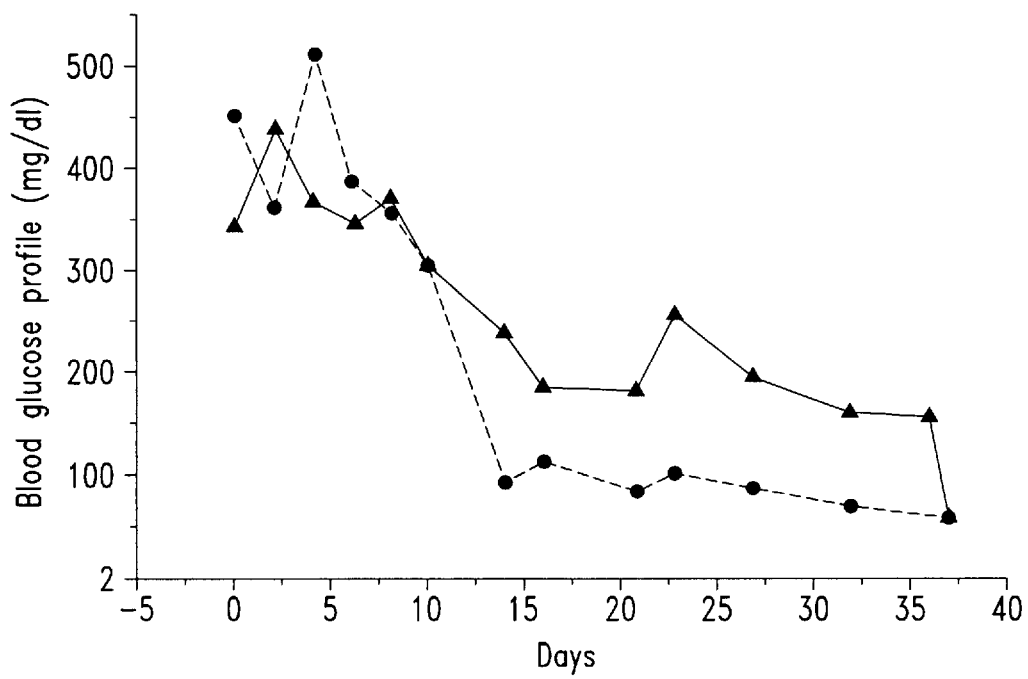
FIG. 13 is a graph in which the levels of glucose in the blood of the diabetic rats which were transplanted with 1350 and 1650 islets just isolated, were measured and were plotted against time in days.

FIGS. 8A and 8B show that the medium used in the present invention enables the islets to grow in all directions. FIG. 9 shows a human islet proliferated in vitro for 8 days using rat islet proliferation methods of the present invention. FIG. 10 shows the increase in DNA content of in vitro proliferating Sprague-Dawley (SD) rat islets against the number of days incubated. FIG. 11A shows fibroblasts growing out from pure islets during proliferation (×100 magnification), and FIGS. 11B and 11C show the fibroblasts removed prior to transplantation (×200 magnification). FIG. 12 shows glucose stimulated insulin secretion from freshly isolated (square) and proliferated (circle) islets. FIG. 13 is a graph of blood glucose (mg/dl) plotted against time in days for 1650 (circle) and 1350 (triangle) fresh rat islets transplanted into the liver of a STZ induced diabetic rat via the hepatic portal vein.

Figure 14:
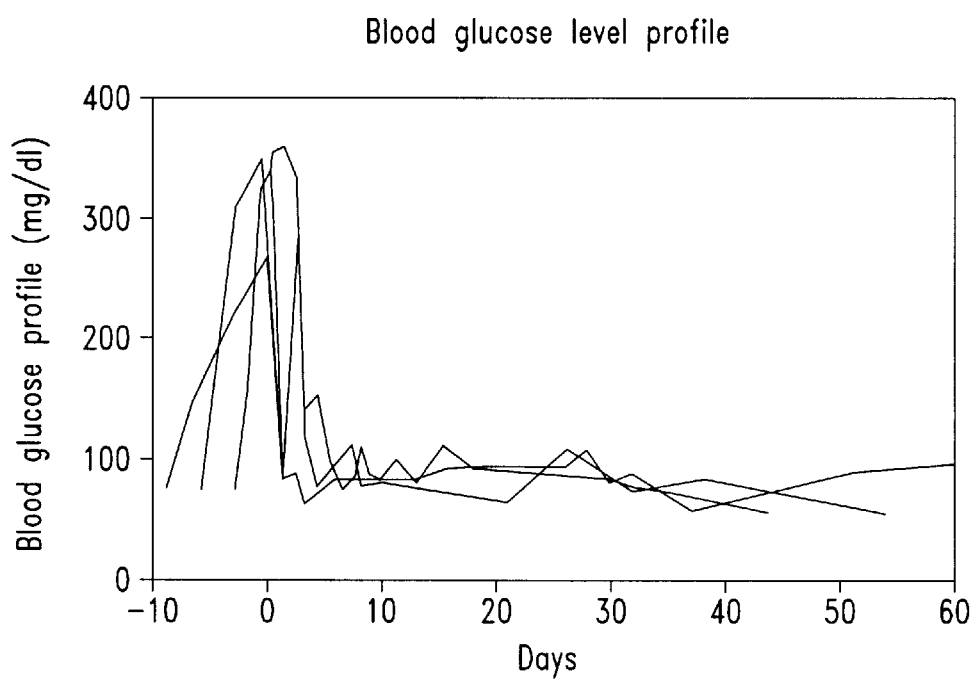
FIG. 14 shows blood glucose level profile of STZ-induced diabetic rat transplanted with 500 proliferated rat islets with days.
Figure 15:
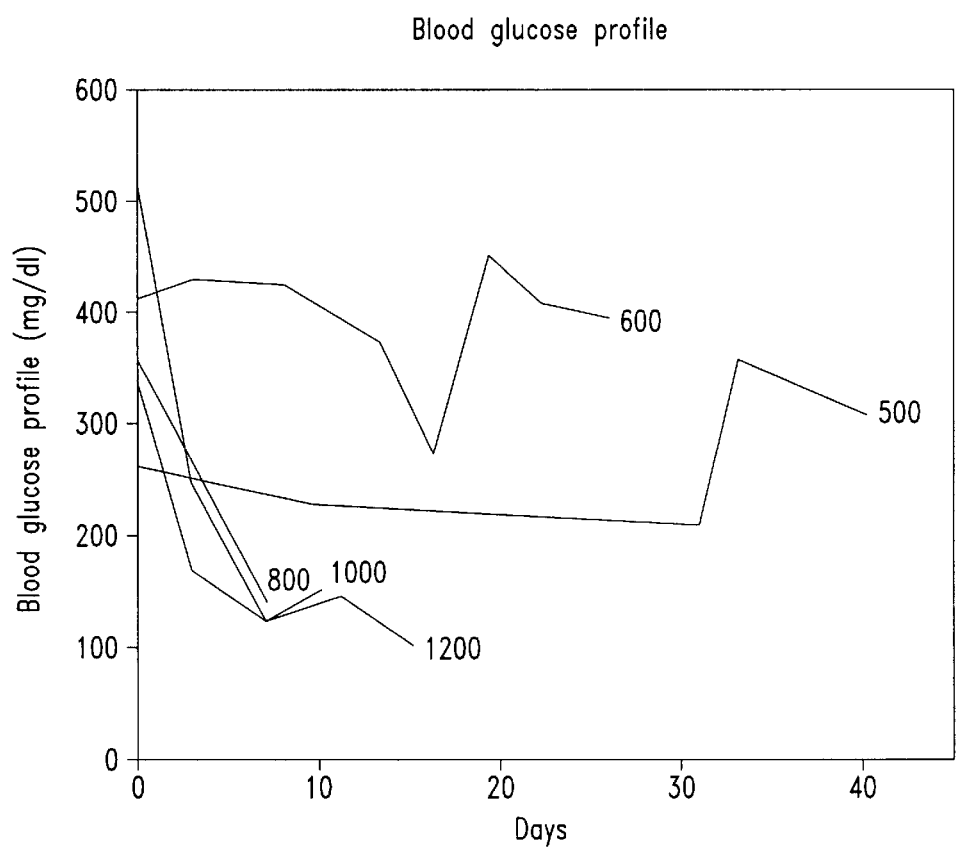
FIG. 15 is a graph of blood glucose (mg/dl) levels against time in days comparing 500, 600, 800, 1000, and 1200 fresh rat islets transplanted into the spleen of STZ-induced diabetic mice, indicating the 800 islets are the minimum islet number required to recover and maintain normoglycaemia.

FIG. 14 is a graph of blood glucose levels (mg/dl) plotted against time in days, 0 being the day of transplant of 500 proliferated rat islets into four (4) rats. FIG. 15 is a graph of blood glucose (mg/dl) levels plotted against the comparing 500, 600, 800, 1000 and 1200 fresh rat islets, respectively, transplanted into the spleen of STZ-induced diabetic mice. The numbers represent the number of islets transplanted. 800 islets are the minimum islet number required to recover and maintain normoglycaemia. The blood glucose levels of the diabetic rats which were transplanted with the Langerhans islets just isolated, were plotted against time in days.

Figure 16:
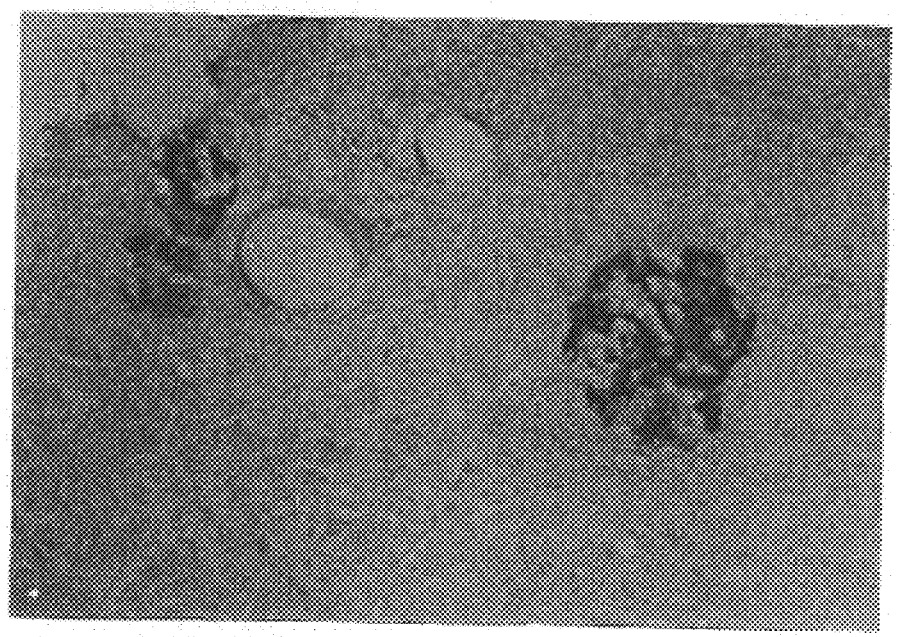
FIG. 16 is a photograph (×200) of a fresh islet transplanted into the spleen of an SZT-induced diabetic nude mouse.

FIG. 16 is a photograph (×200) of a fresh islet transplanted into the spleen of an SZT-induced diabetic nude mouse. The blood glucose concentration recovered and was maintained for 30 days. Then the mouse was sacrificed to collect transplanted islet. The islet was sectioned and stained in an insulin-specific staining method to identify the islet.

FIG. 17 is a graph of blood glucose levels (mg/dl) plotted against time in days comparing different numbers (200, 180, 150) of proliferated islets transplanted into spleens of STZ-induced diabetic mice. Blood glucose levels were measured every other day for several months. The mice used in this experiment had no working immune system; however, in two mice, one with an implanted islet number of 150 and 180, respectively, it is believed that the immune system functioned to the extent that it attacked the implanted islets resulting in the sudden increase in blood glucose level at around day 25.

Figure 18:
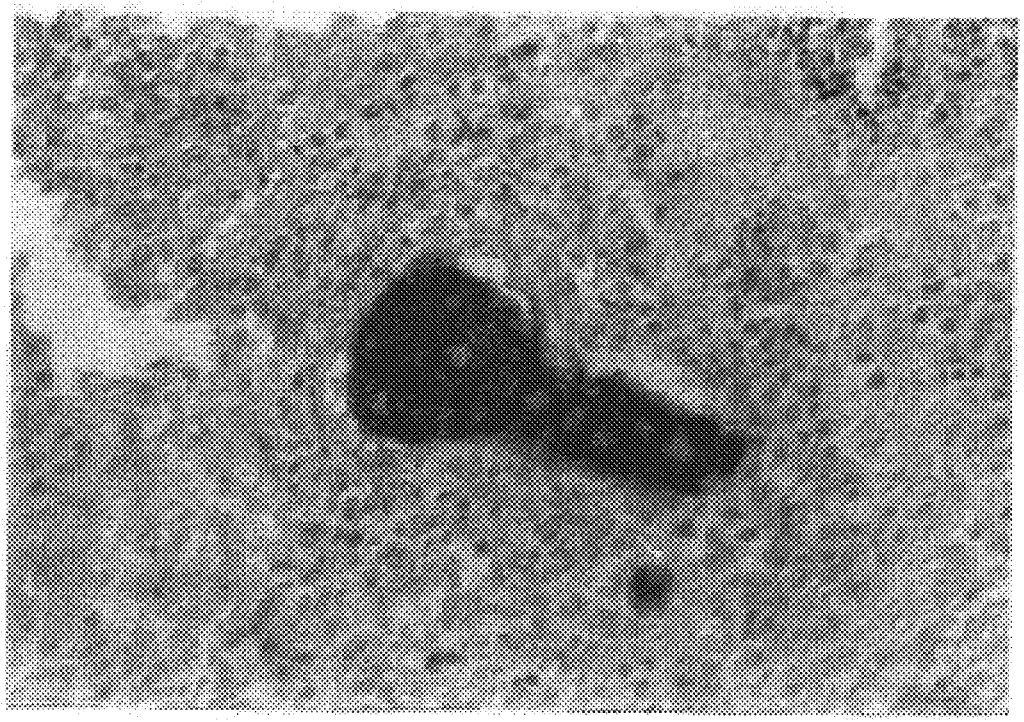
FIG. 18 is a photograph (×400) showing a proliferated islet transplanted into the spleen of STZ-induced diabetic nude mouse.

FIG. 18 is a photograph (×400) showing a proliferated islet transplanted into the spleen of STZ-induced diabetic nude mouse. The mouse recovered and remained normoglycaemia for 3 months. Then the mouse was sacrificed to remove the spleen from the mouse. The spleen was sectioned and stained in insulin-specific staining method to identify the transplanted islet.

Before culturing, the Langerhans islets isolated from the pancreas may be stored. Also, after culturing the proliferated Langerhans islets must be properly stored unless they all are used immediately. To this end, they are preferably frozen in liquid nitrogen.

Dimethyl sulfoxide (DMSO) is useful to protect the Langerhans islets upon freezing. At a convenient or proper time, the frozen stock of the Langerhans islets is thawed for culturing.

In accordance with the present invention, a culture system contains a matrix material in order to provide a three dimensional environment for Langerhans islets. Under this circumstance, the Langerhans islets show a high degree of proliferation. For the matrix material, collagen, complex collagen, tail complex collagen or other biogels (e.g., Matrigel®), or the like, may be used.

The culture medium of the present invention (rat serum for rat islets and human serum would be used for human islets) also contains a radical scavenger which plays the role of protecting the proliferated cells from radical damage. Nicotinamide, mannitol or a superoxide dismutase is added to the culture medium as a radical scavenger.

As mentioned above, the proliferation rate necessary for transplantation must amount to at least 500%. For this, the isolated Langerhans islets are cultured in the presence of growth factors, and cell migrating/scattering factors. Suitable growth factors are selected from the group consisting of insulin transferrin selenite (ITS), epidermal growth factor (EGF), platelet derived growth factor (PDGF), thrombin, progesterone, Linoleic Acid-BSA, pituitary extract and hydrocortisone. Examples of cell migrating/scattering factors include hepatic growth factor (HFG) and tumor promoting activator (TPA).

During culturing, the blood cells go from the Langerhans islets into the medium. As the culturing goes on, the blood cells are subjected to necrosis. Since the blood cells have MHC class II, a major factor which causes the immune rejection upon tissue transplantation, the cultured Langerhans islets can be transplanted in a host with little immune rejection, if any. In the present invention, a cytoskeleton activator is added in the culture medium to enhance islet proliferation. Preferably, anti-integrin β1 antibody is used for this purpose.

A better understanding of the present invention may be obtained in light of the following examples which are set forth to illustrate, but should not be construed to limit the present invention.

EXAMPLE I

Freeze Storage and Thaw of Langerhans Islets 1 ml of 10% fetal calf (bovine) serum (FCS) medium which contained 2,000 (rat) Langerhans islets was added to 0.5 ml of 2M DMSO and allowed to stand at room temperature for 5 min. The procedure of adding DMSO and standing at room temperature was further repeated twice for the first time, with 0.5 ml of 2M DMSO and a period of 25 min., and for the second time, with 0.5 ml of 3M DMSO and a period of 15 min. Thereafter, the medium was allowed to stand for 5 min on ice and then, for 15 min at −7.5° C. This medium was subjected to nucleation using previously chilled forceps and allowed to stand for 15 min at −7.5° C. The temperature was lowered down to −35~40° C. at a rate of 0.2–0.3 per min. Once reaching the temperature, the vial containing the medium was stored in a liquid nitrogen tank.

For thawing, the vial stored in the liquid nitrogen tank was transferred to a cryovial in a water bath of 37° C. until the ice crystals started to thaw. Then, the vial was placed on ice and allowed to stand in order that the Langerhans islets may settle on the bottom. The supernatant was drained out using a Pasteur pipette. The Langerhans islets were added with 10% FCS supplemented with 1 ml of 0.75 M sucrose and allowed to stand on ice for 30 min. Then, the Langerhans islets were added with 1 ml, 2 ml, 4 ml and 8 ml of 10% FCS, successively. After every addition, the Langerhans islets were allowed to stand for 5 min at room temperature. The resulting supernatant was removed and the remaining Langerhans islets were re-suspended in a culture medium and cultured at 37° C. This procedure may be used for rat, mouse, human, and the like, Langerhans islets.

EXAMPLE II

Proliferation of the Langerhans Islets

In this Example, the Langerhans islets which were frozen and thawed as in Example I were used. However, freshly isolated Langerhans islets could also be used as is appreciated by one skilled in the art. During incubation 5% $CO_2$ is added to ambient air.

Serum Preparation

Rat serum was added to medium for proliferating the rat islets. 2–5 ml. blood was obtained from a rat and transferred into sterile 15 ml Falcon tube. The blood was left for 2–4 hours at room temperature and then centrifuged at 3000 g for 10 minutes. The supernatant was transferred to 1.5–2 ml tubes, which were left overnight at 4° C. and then centrifuged again in the same way. The supernatant was stored at −20° C. until use. Human islets were proliferated in the medium containing 10% human serum instead of rat serum that was made in the same way.

The basal medium (50 ml) is prepared by mixing together:
1.1 mg (100 µl) pyrubate, (Gibco brl); 0.25 µg (100 µl) hydrocortisone (Sigma); 100 units/(100 µl) (1 ml) penicillin/streptomycin; 4.456 mg (4 µl) B-mercaptoethanol (Sigma); 14.6 mg L-glutamate (Gibco); 238.3 (1 ml) Hepes Buffer (Gibco); 100 mg (11 mM) glucose (Sigma) plus DMEM to make a volume of 50 ml.

Experiment Example II-I

Culturing of Langerhans Islets Under Basic Conditions

First Day: 500 islets were cultured under basic conditions. The freshly isolated islets were incubated overnight at 37° C.

in 6 ml basal medium supplemented with 600 μl rat serum (10%), 30 μg of insulin-transferrin-sodium selenite (ITS) (5 μg/ml, I-1884, Sigma USA), 6 mg of Linoleic Acid-BSA (1 mg/ml, L-8384, Sigma USA), 60 ng (platelet-derived growth factor), PDGF (10 ngm/ml P8147 Sigma USA), 600 ng thrombin (100 ngm/ml T-4393 Sigma USA), 60 ngm (epidermal growth factor), EGF (10 ngm/ml E-1264 Sigma USA), 187.2 mg of $10^{-4}$ M superoxide dismutase (product no. S-9636, Sigma, USA), 109.32 μg of $10^{-4}$ M mannitol (M-9546 Sigma USA), 61 mg (3 mM) nicotinamide (N-0636 Sigma USA), 12 ng (vascular endothelial growth factor) VeGF (2 ngm/ml V-7259 Sigma USA), 600 ngm (insulin-like growth factor-I and -II) IGF-1 and IGF-2 (I-3769 and I-213P, respectively, Sigma USA).

Experiment Example II-II

Second Day

1. The 500 islets were incubated for 45~120 minutes at room temperature with 50 ng (25 ng/ml) of anti-integrin β1 antibody (Cat. No. I-41720 Transduction Labs. USA) in 2 ml DMEM medium or serum free basal medium.

2. The islets were then suspended in 200 μl of 80 to 100% Matrigelg (Collaborative Biomedical Product, USA) in order to provide a three-dimensional growth environment.

3. Added 2 ml of the above supplemented basal medium and which was also supplemented with 100 μg pituitary extract (50 μg/ml P-1167 Sigma, USA) and cultured for 1–2 days at 37° C.

Experiment Example II-III

Third or Fourth Day

The culture medium was replaced with fresh supplemented basal medium having the same composition as that of the first day except that VeGF is not added and, depending on the islet shape, other factors were added to the medium, as follows:

1. 20 ng (nerve growth factor) NGF (10 ng/ml N-6009 Sigma, USA), 50 ng HGF (25 ng/ml Collaborative Biomedical Product, USA Lot 902287), were added to 2 ml of the supplemented basal medium if the islets became thick and dark in the center of the islet and then the islets were cultured in the medium for 1 or 2 days, or 2. 20 ng NGF and 100 ng anti-integrin β1 antibody (50 ng/ml) were added to 2 ml of the supplemented basal medium if the islets looked spread out and then cultured for 1–2 days.

Observation with a microscope at ×200 magnification was shown in FIG. 9.

After the Sixth or Seventh day, the islets culturing sequence was performed as follows:

Seventh Day

The islets were collected from the 3-dimensional gel. The fibroblasts were removed using dispase by the process described below. The collected islets were cultured overnight in a floating culture, i.e., the islets were not fixed in a medium, such as a gel medium. The culturing medium was 6 ml of the basal supplemented medium, as described above, supplemented with 600 μl of rat serum (10%), 30 μg of insulintransferrin-sodium selenite (ITS), 6 mg of Linoleic Acid-BSA (1 mg/ml), 600 ng thrombin (100 ngm/ml T-4393 Sigma USA), 60 ng EGF, 101 ng nicotinamide, 12 ng VeGF, 600 ng IGF-1, 600 ng IGF-2, 187.2 mg of $10^{-4}$ M superoxide dismutase (Sigma), 109.32 μg of $10^{-4}$ M mannitol.

Eighth Day

1. The islets are incubated in fresh DMEM supplemented with 50 ng of anti-integrin β1 antibody for 14~120 minutes at room temperature.

2. The islets were suspended in Matrigel® to grow in a 3-dimensional environment.

3. 2 ml of the basal supplemented medium was added plus 100 μg pituitary extract and were cultured for 1–2 days at 37° C.

Ninth or Tenth Day

1. Basal supplemented medium added as first prepared, except that VeGF is not used.

2. Depending on the islet shape, the islets were cultured for 2–3 days in the above medium plus the added factors as described in the Third or Fourth Day culture medium.

Fourteenth Day

1. The islets were collected from the gel by using dispase as described below and as done at around the Seventh Day. This step is mainly to release the islets from the gel. However, if any fibroblasts were to remain, they also would be removed from the surface of the islet.

2. The islets were incubated at 37° C. in a floating culture (islets not fixed as in a matrix) in a medium having the same constitutional amounts and components as in the first day. These islets may be transplanted but are preferably subjected to removal as described below.

Experiment Example III

During culturing the amounts of DNA of the Langerhans islets were measured every other day and their relative amounts were plotted for culture times on the basis of the day on which the Langerhans islets were isolated. As seen in FIG. 10, the Langerhans islets proliferated up to about 1,000% on the 14th day after culturing.

EXAMPLE IV

Test for in vivo function of the Langerhans Islets

Experiment Example IV-I

Blood glucose level of diabetic rats transplanted with freshly isolated Langerhans islets.

For this, streptozotocin (STZ) was intraperitoneally injected to the rats at a dosage of 53–55 mg per kg of body weight and the level of glucose in the blood was checked every day for two weeks. If the blood glucose level reached 250 ng/mg, the Sprague-Dawley (SD) rats were judged to be diabetic.

5.5 collagenase X1 (0.7 mg/ml type X1 Sigma, USA) was introduced to the pancreases of healthy rats by injection via the common bile duct to distend the pancreases and to digest them for 17 min. at 37° C.

After the digested pancreas was washed three times with Dulbecco modified Eagle medium (DMEM), the Langerhans islets were isolated therefrom and collected in a discontinuous bovine serum albumin (BSA) concentration gradient method. The collected Langerhans islets were added with DMEM to a final volume of 100–150 μl.

With the aid of 1 ml syringes, the resulting solution was injected into the hepatic portal vein of the diabetic rats anesthetized by intraperitoneal injection of Entobal (Hanlim Pharmacy Co., Ltd., Korea) at a dosage of 60 mg per kg body weight.

1650 (islet equivalents (IEQ) 2750) and 1350 (IEQ 2400) fresh Wistarkyoto (WK) rat islets were transplanted into the livers of 175 g streptozotocin-induced diabetic rats via hepatic portal vein. 1650 fresh islets are enough mass to recover and maintain normoglycaemia but 1350 fresh islets are not enough mass to recover and maintain normoglycaemia, see FIG. 13. Therefore, 1650 fresh islets are minimum required islet number.

Experiment Example IV-I

Blood glucose level after transplantation of ini vitro proliferated rat islets.

The procedure of Experiment Example III-I was repeated using the same Langerhans islets as those of Example II, which were proliferated in a medium supplemented with collagen, radical scavengers, cell migrating/scattering factors, growth factors and anti-integrin β1 antibody.

The blood glucose levels of the rat hosts transplanted with 500 proliferated rat islets were measured and plotted with times. The measurements of the blood glucose level are shown in FIG. 14. As seen, 500 proliferated Langerhans islets completely functioned to recover and maintain normoglycaemia, so that enough insulin was secreted in proper response to the blood glucose levels of the hosts.

Experiment Example IV-III

Blood glucose concentration profile of STZ-induced diabetic mice transplanted with different number of fresh rat islets.

Different numbers of fresh rat islets were transplanted into spleen of STZ-induced diabetic nude mice to determine minimum number of islets required to recover and maintain normoglycaemia. The blood glucose levels of the most mice were measured and plotted with respect to time. The results are given in FIG. 15. The figure shows the profile of blood glucose levels against time in days. At least 800 fresh islets are required to recover and maintain normoglycaemia.

The blood glucose level profile of STZ-induced diabetic mice of FIG. 15 is based on STZ-induced diabetic mice transplanted with proliferated rat islets.

The Langerhans islets isolated from Sprague-Dawley (SD) rats were proliferated in the same medium as in Example II.

About 150–200 proliferated rat islets were transplanted into the spleen of STZ-induced diabetic nude mice. The 150–200 proliferated rat islets are sufficient in number to recover and maintain normoglycaemia.

The islets were transplanted into the spleen of STZ-induced diabetic nude mice. The blood glucose levels of the host mice were measured and plotted against time in days. The results are given in FIG. 17. As compared with FIG. 15, in vitro proliferated (for 5–6 days) islets showed 3–5 fold higher in vivo function than fresh islets.

As described hereinabove, the Langerhans islets, whether they are just isolated from pancreas or thawed from a frozen state, can be proliferated in volume upon culturing in a species similar serum (i.e., rat serum or human serum for rat or human Langerhans islets, respectively) medium further supplemented with radical scavenger, collagen, growth factors and cell migrating/scattering factors. Further, the Langerhans islets which are cultured for a long time in the supplemented medium, are depleted of blood cells, so that they can be transplanted and function well enough to recover and maintain normoglycaemia.

Experiment Example V

In vitro function (glucose response) of proliferated islets.

Fresh and proliferated rat islets were incubated with 2.7 and 16.7 mM glucose for 1 hour and secreted insulin concentration were measured by using 125I-insulin KIT.

Proliferated islets respond nearly null to low glucose concentration and very strongly to high glucose concentration; whereas, fresh islets respond higher to low glucose, lower to high glucose concentration than proliferated islets (as see FIG. 12). The results indicated that in vitro proliferated islets have more desirable functional properties than fresh islets, therefore proliferated islets can be used as autotransplantation material.

Experiment Example IV

Fibroblast Removal

Fresh islets are likely to be contaminated with fibroblasts even though they are collected in a pure state as can be seen by the fact that many fibroblasts grow out from the islets during the proliferation. The fibroblasts are removed completely prior to islet transplantation, as seen in FIG. 11C. Islets are dispersed in a gel (e.g., Matrigel®) during proliferation. At about the seventh or fourteenth day, the islets are collected from the gel and 400 μl of dispase (Collaborative Biomedical Products, USA, Cat. 40235) is added and incubated for about 10 minutes at 37° C. Then the islets are aspirated back and forth several times causing the gel acted on by the dispase to be removed from the islets which exposes the fibroblasts to the force created during the back and forth aspiration causing the fibroblasts to become separated from the surface of the islets to prepare fibroblast-free islets.

Islets proliferated up to 5- and 10- fold for the first and second week during in vitro culturing, respectively. These proliferated islets showed a more desirable in vitro glucose-response pattern than fresh islets. Their transplantation results showed that those islets have a 3~4 fold higher capability to recover and maintain normoglycaemia than fresh islets. These data suggest that in vitro proliferated islets are a better source than fresh islets for transplantation to treat diabetes. Consequently, the present invention can produce a large quantity of the Langerhans islets and, thus, transplantation using the proliferated islets according to the present invention is a promising therapeutic means for the treatment of diabetes.

Experiment Example VII

Islet Autotransplantation-stimulated Islet Regeneration

Islet autotransplantation recovered and maintained normoglycaemia. In the diabetic rats, islet neogenesis did appear. Exogenous insulin injection also did not stimulate islet neogenesis. However, islet autotransplantation stimulates islet neogenesis.

The following table shows insulin content, number, size of islets collected from rats and rice which were either pancreatectomized (columns 2 and 3) or transplanted into diabetic mice/rats after transplantation (columns 4, 5 and 6). The islets used were either fresh (columns 4 and 5) or cultured/proliferated for 6 days (column 6) according to the process of the present invention. The transplantation (TX) was islet auto-transplantation. The results in columns 5 and 6 indicate that the transplanted islets, either fresh or proliferated according to the present invention result in islet regeneration in the pancreas.

| | 80–90% pancreatectomy on day 0 | 2 months after 90% pancreatectomy | 25 day unstable blood glucose level after 1350 islet TX in liver | 25 day stable normolglycaemia controlled by 1650 fresh after TX in liver | 13 month normoglycaemia after 500 proliferated islets TX in liver |
|---|---|---|---|---|---|
| Pancreatectomy/fresh/fresh/autotransplantation | | | | | |
| Collected islet number | 113 (EQ 223) | 235 (EQ 505) | 70 (IEQ 100) from panc. | 226 (IEQ 168) from panc. | 164 (IEQ 264) from panc. |
| islet size | no data collected since normal | Very large | very small to very large | small islet (90~119) immature | Very large |
| insulin present | High | High | High | Low | High |

The following experimental results prove this (see Table, above)

1. 1350 fresh rat islets were transplanted into the liver of a STZ-induced diabetic rat via hepatic portal vein. Blood glucose concentration declined gradually to be normoglycaemia 35 days later. The values lingered in the 200's for 20 days and finally normoglycaemia for 1–2 days, as seen in FIG. 13. Islets were collected from the pancreas and stained deeply with dithizone.

2. 1650 fresh rat islets were transplanted syngeneically into the liver of a STZ-induced diabetic rat. The rat recovered normoglycaemia and maintained it for 25 days, as seen in FIG. 13. After sacrificing, 226 (EQ 168) small islets were collected and were not stained with dithizone. The pancreas islets were immature and could be produced by neogenesis. In conclusion, on comparing both cases, islet autotransplantation-recovered normoglycaemia seems to provide a favorable environment for islet neogenesis and replication by secreting various natural substances.

3. The rats transplanted syngeneically with 500 proliferated islets maintained normoglycaemia for 13 months. 164 large islets (IEQ 264) were collected and stained deeply with dithizone. The results indicates that neogenic (pancreas) islets grew up to large mature islets over a long period of time and islet autotransplantation enhances islet regeneration and stimulates islet maturation.

4. 90% pancreatectomy rat maintained normoglycaemia for 2 months. 235 large islets were collected from the remaining pancreas. The islets were stained deeply with dithizone. They seemed to originate from islet regeneration and grew for 2 months.

5. 90% pancreatectomy rat maintained normoglycaemia for 2 days. Islets were collected from the remaining pancreas.

6. In 90% pancreatectomy rat, 113 (IEQ 223) islets are collected from the remaining head part of the pancreas on the day of the pancreatectomy. On the basis of the pancreatectomy results, islet regeneration rate and size depends on the magnitude of islet deficiency.

Islet proliferation research is performed for the ultimate purpose of treating a diabetic patient by islet autotransplantation by providing a sufficient number of islets for transplant. The present invention provides the required number of islets since it enables successful islet proliferation in vitro. That is, one of the major reasons for the failure of transplantation is an insufficient number of islets are available for transplant into a diabetic patient. This problem is overcome by the present invention.

While the present invention was developed using rat and mice islets, the application of the present invention to proliferate human islets is within the scope of the teachings of the present invention, as can be appreciated by those skilled in the art.

The present invention has been described in an illustrative manner so as to be easily understood by one skilled in the art. This description, examples and illustrations are intended to be in the nature of the description rather than of a limitation, as appreciated by those skilled in this art. Many modifications and variations of the present invention are possible in light of the above teachings. Therefore, it is to be understood that within the scope of the appended claims, the invention may be practiced otherwise than as specifically described.

What is claimed is:

1. A method for in vitro culturing and proliferating isolated Langerhans islets endocrine cells so as to be suitable for transplantation comprising:

providing fresh viable Langerhans islets endocrine cells including cells capable of differentiating into insulin producing cells;

providing a first culturing medium comprising a basal medium supplemented with serum, at least one radical scavenger selected from the group consisting of nicotinamide, mannitol or superoxide dismutase; at least one growth factor selected from the group consisting of: insulin transferring selenite (ITS), epidermal growth factor (EGF), platelet derived growth factor (PDGF), thrombin, Linoleic Acid-BSA, hydrocortisone and progesterone; and at least one antinecrosis or antiapoptosis factor selected from the group consisting of insulin-like growth factor-I (IGF 1) and II (IGF 2), vascular endothelial growth factor (VeGF);

culturing the Langerhans islets endocrine cells including cells capable of differentiating into insulin producing cells for a period of about one day in the first culturing medium to form a first culture growth;

collecting the first culture growth and incubating at room temperature in serum-free Dulbecco modified Eagle medium (DMEM) with anti-integrin β1 antibody or serum free basal medium with anti-integrin β1 antibody for 45–120 minutes to form a second culture growth;

suspending the second culture growth in a matrix material to provide a 3 dimensional culture growth environment and adding a second culturing medium comprising the first culturing medium and further including, at least, pituitary extract and then culturing for 1 or 2 days to provide a third culture growth dispersed in the matrix material;

providing a third culturing medium for culturing the third culture growth in the matrix material, the third culturing medium comprising the second culturing medium without VeGF, and optionally adding to the third culturing medium nerve growth factor (NGF) and hepatocyte growth factor (HGF) if the islets of the third culture growth are thick relative to the fresh islets and the center of the islets are dark relative to the fresh islets, or optionally adding to the third culturing medium NGF and anti-integrin β1 antibody if the islets are spread out and culturing for a period of about one or two days to form a fourth culture growth;

collecting the islets from the matrix material and adding an enzyme to the collected islets and to the matrix material containing islets and incubating for about 10 minutes to provide an incubated product; and aspirating the incubated product back and forth numerous times causing the matrix material acted on by the enzyme to be removed from the islets thereby exposing the fibroblasts to the force created during the back and forth aspiration causing the fibroblasts to become separated from the surface of the islets to prepare fibroblast free islets.

2. The method of claim 1, further providing a fourth culturing medium comprising the basal medium supplemented with serum, insulin-transferrin-sodium selenite (ITS), Linoleic Acid-BSA, thrombin, EGF, nicotinamide, VeGF, IGF-1, IGF-2, superoxide dismutase and mannitol;

culturing the fibroblast free islets for about an 8–12 hours to provide a fifth culture growth;

providing a fifth culturing medium comprising DMEM with anti-integrin β1 antibody and culturing the fifth culture growth for 45–120 minutes at room temperature to form a sixth culture growth;

suspending the sixth culture growth in a matrix material to provide a 3 dimensional culture growth environment and adding a sixth culturing medium comprising the first culturing medium and further including, at least, pituitary extract and then culturing for 1 or 2 days to provide a seventh culture growth dispersed in the matrix material;

providing a seventh culturing medium for culturing the seventh culture growth dispersed in the matrix material, the seventh culturing medium comprising the second culturing medium without VeGF, and optionally adding to the third culturing medium NGF and HGF if the islets of the third culture growth are thick and the center of the islets are dark, or optionally adding to the third culturing medium NGF and anti-integrin β1 antibody if the islets are spread out and culturing for a period of about one or two days to form an eighth culture growth; and collecting the islets from the matrix material and adding an enzyme to the collected islets and to the matrix material containing islets and incubating for about 10 minutes to provide an incubated product; and aspirating the incubated product back and forth numerous times causing the matrix material acted on by the enzyme to be removed from the islets thereby exposing the fibroblasts to the force created during the back and forth aspiration causing the fibroblasts to become separated from the surface of the islets to prepare an increased number of fibroblast free islets.

3. The method of claim 1 wherein the serum is obtained from the same species as that of the Langerhans islets.

4. The method of claim 1 wherein the Langerhans islets are either from a rat and the serum used is about 10% rat serum or are from a human and the serum used is about 10% human serum.

5. The method of claim 1 wherein the viable Langerhans islets endocrine cells including cells capable of differentiating into insulin producing cells for proliferation are derived from a patient for autotransplantation.

* * * * *